United States Patent [19]

Polikoff

[11] 4,387,707

[45] Jun. 14, 1983

[54] EYE TREATMENT DEVICE AND METHOD

[76] Inventor: Lawrence A. Polikoff, 2831 Medill Pl., Los Angeles, Calif. 90064

[21] Appl. No.: 263,852

[22] Filed: May 14, 1981

[51] Int. Cl.³ ............................................. A61H 1/02
[52] U.S. Cl. ................................................... 128/25 A
[58] Field of Search ..................... 128/25 R, 25 A, 64, 128/76.5, 163, 249, 65

[56] References Cited

U.S. PATENT DOCUMENTS

| | | | |
|---|---|---|---|
| 893,021 | 7/1908 | Siebert, Jr. | 128/64 |
| 2,114,407 | 4/1938 | Tsumura | 128/25 A |
| 2,708,928 | 5/1955 | Zenatti | 128/25 A |
| 3,848,607 | 11/1974 | St. Clair | 128/64 |

Primary Examiner—John D. Yasko
Attorney, Agent, or Firm—William P. Green

[57] ABSTRACT

An eye treatment device including a unit adapted to be placed against a user's eye and forming a chamber which contains a fluid maintained under a fluctuating pressure, with the chamber having a flexible wall to be received adjacent the eye and communicate the fluctuating pressure thereto in a manner exerting a fluctuating massaging force against the eye through the flexible wall. To correct a user's vision, the eye may first be massaged by the described device, or otherwise, to soften the eye, following which a shaping element may be placed against the eye to deform it slightly to a changed contour improving the vision in a desired respect.

9 Claims, 5 Drawing Figures

EYE TREATMENT DEVICE AND METHOD

BACKGROUND OF THE INVENTION

This invention relates to an improved apparatus and methods for treating a person's eyes by massage.

The internal pressure within a person's eye can be reduced by massaging the eye in a manner causing the flow of aqueous fluid from within the eye. U.S. Pat. No. 793,004 discloses an eye massage machine in which an element is forcibly vibrated by a mechanical vibrating unit connected to the center of the element to exert a massaging action against the eye. U.S. Pat. No. 2,690,173 shows a device having an eye contacting member to which a pneumatic pressure is applied to maintain the eye under pressure while the eye is exercised. U.S. Pat. No. 2,555,636 shows a device in which pressurized fluid is applied directly to the eye.

SUMMARY OF THE INVENTION

One object of the present invention is to provide a device which is capable of applying an improved type of massaging force to a user's eye, with the intention of reducing the internal pressure in the eye to combat a glaucoma condition or to attain other desirable results. A device embodying the invention includes a unit to be placed against a user's eye and containing a chamber having a flexible wall which at one side is exposed to the pressure of a fluid contained in the chamber, and at its opposite side contacts a user's eye to communicate the fluid pressure thereto. In conjunction with the eye contacting unit, the device includes means for applying a fluctuating pressure to the fluid in the chamber, so that the force exerted against the eye is a correspondingly fluctuating repeatedly increasing and decreasing massaging force. The flexible wall may be formed as a thin diaphragm of rubber, resinous plastic material, or the like, peripherally secured to a hollow body of the eye contacting unit and preferably adapted to deform to a concave configuration following the contour of the contacted eye. The hollow body of the unit may have a rear opening across which the flexible wall extends, with the edges of the body which extend about that opening being curved in correspondence with the curvature of an eye.

The fluctuating pressure may be developed by a motor driven pumping unit, desirably a reciprocating piston and cylinder type pump producing intermittent pressure peaks with reduced pressure intervals therebetween. The fluid pumped by this unit may be either a liquid or gas, but in most instances is preferably a liquid, which by virtue of its essential incompressiblity can apply the desired fluctuating pressure most effectively to the flexible eye contacting wall. The liquid may gradually discharge from the pressurized chamber of the device through an outlet which is sufficiently restricted to assure application of fluctuating pressure as desired to the flexible wall and through that wall to the eye.

The eye contacting unit may be held against the eye by means attachable to the user's head, such as by a strap extending about the head and carrying the eye contacting unit. If two of the user's eyes require treatment, there may be two such units carred by the strap or other mounting means in spaced relation.

A further object of the invention is to provide an improved method for correcting or partially correcting the vision in a user's eyes. This result is achieved by a novel process which combines the effects of massage with a forced deformation of the eye to a changed contour. Specifically, the eye is first massaged by the above discussed device or other equipment, or manually if preferred, to induce a flow of aqueous fluid from and thereby soften the eye, following which I place against the eye a contact lens or other shaping part having an eye contacting surface different than the intial contour of the engaged part of the eye and adapted to forcibly reshape the eye to a predetermined changed configuration. While contact lenses have been used in the past to reshape an eye, I do not know of any prior instance in which the effect has been enhanced by first massaging the eye to soften it and thereby render the eye more susceptible to deformation.

BRIEF DESCRIPTION OF THE DRAWINGS

The above and other features and objects of the invention will be better understood from the following detailed description of the typical embodiment illustrated in the accompanying drawings in which.

DESCRIPTION OF THE PREFERRED EMBODIMENT

Figures 1, 2, 3, 4:
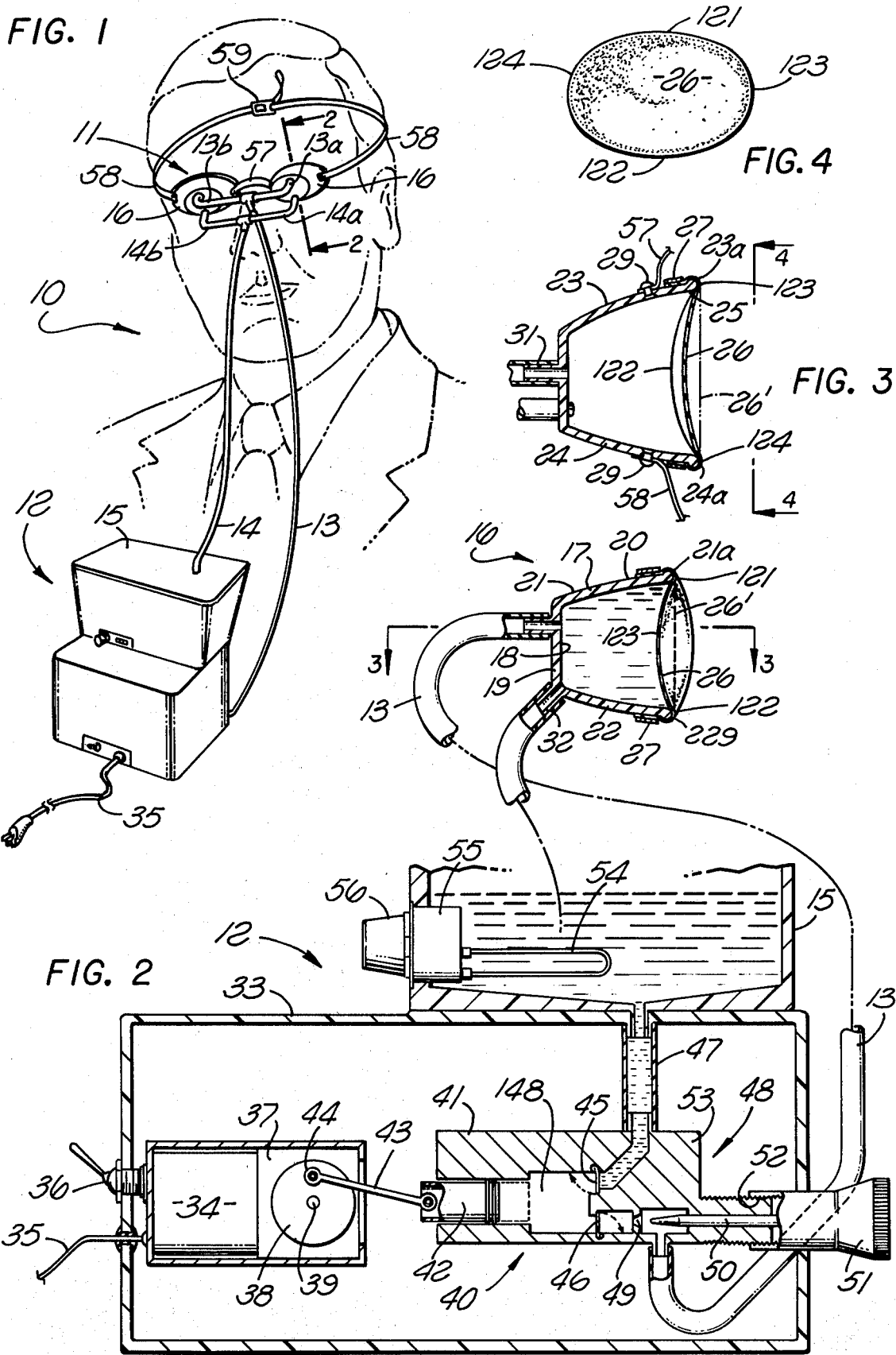
FIG. 1 is a somewhat diagrammatic perspective representation of an eye massaging device constructed in accordance with the invention.
FIG. 2 is a central vertical section through one of the eye massaging units of the device, taken on line 2—2 of FIG. 1, and illustrating diagrammatically the associated pumping unit.
FIG. 3 is a horizontal section taken on line 3—3 of FIG. 2.
FIG. 4 is a view taken on line 4—4 of FIG. 3.

The eye massaging device 10 illustrated in FIG. 1 includes an assembly 11 to be applied to a user's head and contact his eyes, and a pumping device 12 for delivering water under fluctuating pressure to assembly 11. The pressurized water flows from the fluid source 12 to assembly 11 through a flexible hose 13, and may return from assembly 11 through a second flexible hose 14 into a water reservoir 15 forming the upper portion of pumping device 12.

Assembly 11 includes two typically identical units 16 to be received against and apply massaging force to the user's two eyes respectively. These units 16 may be connected together by a short strap 57, and be retained on the user's head by two additional longer straps 58, attached to the units 16 respectively and detachably connectable together at the back of the user's head. The end of one of the straps 58 may carry a buckle 59, while the end of the other strap 58 may be attachable adjustably to the buckle to tighten the device on the user's head. The straps 57 and 58 may be secured to units 16 in any convenient manner, as by rivets or other fasteners represented at 29.

As seen best in FIGS. 2 and 3, each of the units 16 includes a typically essentially rigid hollow body 17 containing a chamber 18 within which water delivered from the device 12 is contained. Body 17 has a generally vertical front wall 19 and a peripheral wall 20 extending rearwardly from the edge of front wall 19 entirely about chamber 18 and forming top and bottom walls 21 and 22 (FIG. 2) and opposite side walls 23 and 24 (FIG. 3).

The rear edges or extremities 21a, 22a, 23a and 24a of these walls 21, 22, 23 and 24 form an opening 25 at the back side of body 17 which may have the approximately oval outline configuration illustrated in FIG. 4. This rear opening 25 is closed by a flexible diaphragm or wall 26, which functions as the rear wall of chamber 18, and is exposed at its forward side to the pressure of water contained in that chamber. The rear side of diaphragm 26 is placed in contact with the front of a user's eye, with the eyelid closed, and is capable of then automatically assuming the concavely curved or recessed configuration illustrated in FIGS. 2 and 3 conforming to and following the contour of the convex front surface of the eye. Diaphragm 26 is thus capable of communicating the pressure of water within chamber 18 to the front of the eyelid over substantially the entire area of the eye.

Diaphragm 26 may be attached to body 17 in any convenient manner, as by extension of the peripheral edge of diaphragm 26 rearwardly along the outer surfaces of walls 21 through 24 of body 17, with a clamp 27 being tightened about the edge of diaphragm 26 to hold it tightly against the various walls of body 17 in a manner forming a continuous generally annular seal between the edge of the diaphragm and the carrying body. To avoid damage to diaphragm 26, the various rear edge surfaces 21a, 22a, 23a and 24a of body 17 may be of rounded sectional configuration as illustrated in FIGS. 2 and 3.

In addition to its flexiblity to conform to the contour of the front of the eye, diaphgram 26 preferably also is elastic, and may normally tend by its resilience to return to a condition such as that represented in broken lines at 26, in FIGS. 2 and 3. For best results, diaphragm 26 may be formed of a thin sheet of surgical rubber or other elastomeric material capable of withstanding repeated slight flexing in use as the eyes are massaged. Alternatively, the diaphragm may be formed of a thin film of fully flexible resinous plastic material.

As seen in FIGS. 2 and 3, the rear edges 21a, 22a, 23a and 24a of body 17 which define rear opening 25 may curve gradually forwardly and rearwardly as they advance about the periphery of the opening in a manner following the curvature of the eye and enabling optimal contact of the diaphragm 26 with the eye. More particularly, as seen in FIG. 2, the peripheral edge in advancing from a top central location 121 to a bottom central location 122 may first advance gradually rearwardly to a side central location 123, and then curve gradually forwardly to the bottom central location 122. At the opposite side of opening 25, the rear edge of body 17 has the same configuration to curve gradually rearwardly to a second vertically central side location 124, and then gradually return forwardly to the top central location 121. The rear edge of the body thus has the configuration illustrated in FIG. 2 as viewed from either side, and has the curvature illustrated in FIG. 3 as seen in either top or bottom plan view.

Water supply hose 13 may be connected to bodies 17 by forming hose 13 to have two branches 13a and 13b whose ends are receivable about and frictionally connectable to tubular inlets 31 formed on bodies 17. Similar outlet tubes 32 formed on bodies 17 may be connectable to two branches 14a and 14b of water discharge tube 14.

Pumping device 12, which is illustrated very diagrammatically in FIG. 2, may include a bottom housing 33 to the upper side of which the top water receptacle or supply container 15 is mounted. An electric motor 34 within housing 33 may be driven by 120 volt A.C. line current delivered through an electrical cord 35 under the control of an on/off switch 36. Motor 34 may carry a reduction gear 37 driving an element 38 rotatively about an axis 39 at a speed slower than the rate of rotation of the main drive shaft of the motor. This rotating element 39 then drives a reciprocating piston and cylinder type pump 40 for pumping water from receptacle 15 and discharging it at a repeatedly and rapidly fluctuating slightly super-atmospheric pressure to the units 16 through line 13.

Pump 40 includes a cylinder 41 containing a piston 42 which is reciprocated within the cylinder in response to rotation of part 38 by the motor. This reciprocation may be attained by any convenient type of drive, typically illustrated as a connector rod 43 pivotally attached at one end to the piston and pivotally connected at its opposite end 44 to rotating element 38 at an eccentric location.

The cylinder has spring pressed inlet and outlet check valves represented diagrammatically at 45 and 46 in FIG. 2, enabling the piston on a leftward stroke to draw water from receptacle 15 through a hose 47 past inlet valve 45 into chamber 148, and on a rightward returning stroke to force that water past discharge check valve 46 and into hose 13 leading to chambers 18 of eye contacting units 16. A substantial pressure is thus developed in line 13 and chambers 18 upon each rightward pumping stroke, and during the leftward intake stroke of piston 42 that pressure is interrupted, to thereby repeatedly increase and decrease the pressure in chambers 18.

The rate and pressure at which water can be delivered into line 13 can be varied by manual adjustment of a regulating valve 48 which offers a controlled and adjustable restriction to the rate of flow through that valve. This valve may include means forming an orifice 49 through which the water discharging from the cylinder flows, and a needle valve 50 movable into and out of that orifice to differently adjusted positions in accordance with rotation of control knob 51. This knob 51 may have a threaded connection 52 to the body 53 of valve 48, with that threaded attachment causing rightward and leftward adjusting movement in response to rotation of the knob 51 and carried needle valve 50. Adjustment of valve 48 thus varies the maximum pressure attained in chambers 18 during the rightward strokes of piston 24, typically between about 25 and 150 p.s.i., with the minimum pressure between pumping strokes typically falling to about 15 p.s.i.

The water delivered to each eye contacting unit 16 may be heated to a controlled temperature giving the apparatus a capacity for warming the eyes during the massaging process. For this purpose, an electric heating element 54 may be provided within reservoir 15, in contact with the water, and may be controlled by a thermostat 55 capable of maintaining the water at any desired super-ambient temperature to which a manually actuable control knob 56 may be set.

In placing the device in use, a first step is to fill water into supply receptacle 15, following which a user positions the two eye contacting units 16 in engagement with his eyes and then retains them in that position by tightening straps 58 on his head. He may then turn the motor on by actuating switch 36, to commence reciprocating movement of piston 42 acting to pump water from receptacle 15 through the cylinder and line 13 into chambers 18 of the two eye contacting units 16. The pressure fluctuates repeatedly and rapidly between a maximum pressure attained during rightward movement of the piston and a reduced pressure attained during each leftward stroke of the piston. The restriction formed by discharge line 14 from units 16 offers sufficient resistance to the flow of the water from chambers 18 to assure a substantial repeated fluctuation of pressure within each of those chambers. This pressure is applied through the rear flexible walls 26 of the chambers to the user's eyes, over substantially the entire areas of the accessible portions of those eyes. The resulting continual massaging action tends to cause an increased flow of aqueous fluid from the interior of the eye in a manner reducing the internal pressure of the eye. The fluctuation of pressure can be varied by adjustment of valve 48, to optimize the effect for a particular individual.

Figure 5:
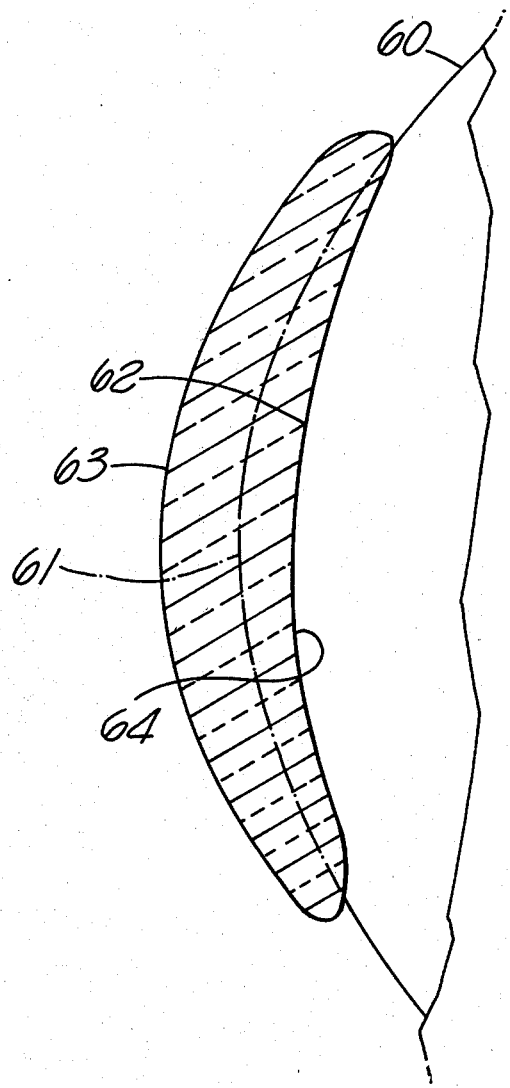
FIG. 5 illustrates somewhat diagrammatically a step in the correction of a person's eyesight by the method of the present invention.

After the eye has been massaged in this way, the softened condition of the front surface of the eyeball resulting from the reduction in internal pressure renders it especially susceptible to controlled reshaping by placement of a contact lens or the like on the softened eye to cause it to assume a predetermined contour built into that lens. This method of correcting for a visual defect is illustrated in FIG. 5, in which the front surface of a user's eyeball is represented at 60, with the inital contour of that surface being shown in broken lines at 61. If it is assumed that the eye is myopic or nearsighted, in that broken line condition, correction of the nearsightedness can be attained by deforming the front surface of the eye to a less convex configuration such as that represented in full lines at 62 in FIG. 5. This is achieved in accordance with the present invention by first massaging and thereby softening the eyeball and then placing a contact lens or other shaping element 63 against the softened eye. The inner or rear surface 64 of this element is concave but at a curvature less than the initial curvature of the eye, and predetermined to give the engaged eye the desired changed shape shown in full lines in FIG. 5. The lens may be left on the softened eye for an extended period of time tending to retain the eye permanently in the changed shape in which the defect in vision is corrected. The entire treatment can be repeated as many times and as often as necessary to achieve the desired final result. Other abnormalities such as astigmatism can similarly be corrected by appropriately designing the reshaping lens or element 63.

While a certain specific embodiment of the present invention has been disclosed as typical, the invention is of course not limited to this particular form, but rather is applicable broadly to all such variations as fall within thescope of the appended claims.

I claim:

1. An eye treatment device comprising:
   a unit to be placed against the eye and forming a chamber containing a liquid under pressure;
   said chamber having a flexible wall exposed at one side to the pressure of said liquid and whose opposite side is adapted to be received adjacent the eye and to communicate the pressure of said liquid thereto; and
   means for applying to said liquid in the chamber a pressure which fluctuates to exert a fluctuating massaging force to the eye through said flexible wall;
   said flexible wall being constructed and adapted, when said opposite side thereof is placed against the eye, to assume a concave curvature at said opposite side conforming to the eye to apply said massaging force over a substantial area of the eye.

2. An eye treatment device as recited in claim 1, in which said unit includes a hollow body to be received in front of the eye and having a rear opening across which said flexible wall extends, said body having rear edges which are curved to follow essentially the curvature of an eye against which the unit is placed.

3. An eye treatment device as recited in claim 1, in which said means for applying said fluctuating pressure to the liquid includes a motor driven pumping device producing said fluctuating pressure.

4. An eye treatment device as recited in claim 1, including means for holding said unit on a user's head and against his eye.

5. An eye treatment device as recited in claim 1, including means for heating said liquid to warm the eye.

6. An eye treatment device as recited in claim 5, in which there are two of said units to be placed against the two eyes respectively of a user and each including a body forming a liquid containing chamber and carrying a flexible wall for communicating pressure to the eye, with said means comprising a motor driven pump applying fluctuating liquid pressure to said chambers of both of said units, said body of each unit having an edge extending about said flexible wall and curving to follow essentially the curvature of an eye against which the device is placed.

7. The method of treating an eye that comprises:
   placing a flexible diaphragm in front of the eye with the diaphragm curved concavely in conformance with the curvature of the eye;
   applying a fluctuating pressure to fluid located in front of and contacting the diaphragm; and
   communicating said fluctuating pressure from said fluid through said diaphragm to the eye.

8. The method as recited in claim 7, in which said fluid is a liquid.

9. The method as recited in claim 7, including maintaining said fluid at a super-ambient temperature during application of said fluctuating pressure thereto to simultaneously warm the eye.

* * * * *